United States Patent [19]

Lago

[11] 4,025,571

[45] May 24, 1977

[54] MANUFACTURE OF HYDROCARBONS

[75] Inventor: Rudolph M. Lago, Yardley, Pa.

[73] Assignee: Mobil Oil Corporation, New York, N.Y.

[22] Filed: May 12, 1976

[21] Appl. No.: 685,870

[52] U.S. Cl. .................. 260/668 D; 252/477 R; 260/668 R; 260/682; 423/328; 208/DIG. 2

[51] Int. Cl.² ................................. C07C 1/20

[58] Field of Search .......... 260/668 R, 668 D, 682; 423/328; 208/135, DIG. 2

[56] References Cited

UNITED STATES PATENTS

| | | | |
|---|---|---|---|
| 3,140,249 | 7/1964 | Plank et al. ............... | 208/120 |
| 3,140,251 | 7/1964 | Plank et al. ............... | 208/120 |
| 3,178,365 | 4/1965 | Miale ......................... | 208/120 |
| 3,728,408 | 4/1973 | Tobias ....................... | 260/668 C |
| 3,894,103 | 7/1975 | Chang et al. ............... | 260/668 R |
| 3,894,105 | 7/1975 | Chang et al. ............... | 260/668 R |
| 3,894,106 | 7/1975 | Chang et al. ............... | 260/668 R |
| 3,894,107 | 7/1975 | Chang et al. ............... | 260/668 R |
| 3,928,483 | 12/1975 | Chang et al. ............... | 260/668 R |
| 3,979,472 | 9/1976 | Butter ......................... | 260/668 R |

Primary Examiner—Veronica O'Keefe
Attorney, Agent, or Firm—Charles A. Huggett; Raymond W. Barclay

[57] ABSTRACT

A catalytic process is provided for converting a $C_1$–$C_4$ monohydric alcohol, an ether derived from said alcohol or a mixture of such alcohol and ether to a hydrocarbon mixture rich in $C_2$–$C_3$ olefins and mononuclear aromatics with high selectivity for para-xylene production by contact, under conversion conditions, with a catalyst comprising a crystalline aluminosilicate zeolite having a crystal size of at least about 1 micron, a silica to alumina ratio of at least about 12 and a constraint index, as hereinafter defined, within the approximate range of 1 to 12.

9 Claims, No Drawings

MANUFACTURE OF HYDROCARBONS

BACKGROUND OF THE INVENTION

1. Field of the Invention

This invention relates to a process for the conversion of low molecular weight monohydric alcohols or ethers to olefinic and aromatic hydrocarbons in the presence of a specified crystalline aluminosilicate zeolite catalyst characterized by a crystal size of at least about 1 micron.

2. Description of the Prior Art.

A remarkable growth in the production of synthetic fibers, plastics and rubber has taken place in recent decades. This growth, to a very large extent, has been supported and encouraged by an expanding supply of inexpensive petrochemical raw materials such as ethylene, benzene, toluene and xylenes. Accompanying this remarkable development there has been an increasing demand for aromatic hydrocarbons for use as high octane gasoline components. Environmental factors which limit the lead content of gasoline are likely to aggravate the need for aromatics.

Increasing demand for olefins, e.g. $C_2$–$C_3$ olefins and for aromatic hydrocarbons, e.g. para-xylene, has, from time to time, led to periods of shortage, either due to a diminished supply of suitable feedstocks or to limited processing capacity. In any event, it would appear desirable to provide efficient means for converting raw materials other than petroleum to olefins and aromatic hydrocarbons.

Of the latter type compounds, xylenes are representative of a valuable fraction. Of the xylene isomers, i.e. ortho-, meta- and para-xylene, meta-xylene is the least desired product, with ortho- and para-xylene being the more desired products. Para-xylene is of particular value being useful in the manufacture of terephthalic acid which is an intermediate in the manufacture of synthetic fibers such as "Dacron".

SUMMARY OF THE INVENTION

In accordance with the present invention, there has been discovered a process which simultaneously produces both valuable light olefinic hydrocarbons and mononuclear aromatics with high selectivity for para-xylene production. The present process involves conversion of lower monohydric alcohols having up to four carbon atoms, their ether derivatives or mixtures of any of these by contact at elevated temperatures with a catalyst comprising a crystalline aluminosilicate zeolite having a crystal size of at least about 1 micron, usually in the approximate range of 1–20 microns and preferably 1–6 microns. The crystalline aluminosilicate zeolite is essentially characterized by a silica to alumina ratio of at least about 12 and a constraint index within the approximate range of 1 to 12 to yield a reaction product mixture comprising light olefins, monocyclic aromatic hydrocarbons and water and recovering the said hydrocarbons.

The alcohols may be manufactured from synthesis gas, i.e. a mixture of CO and $H_2$, from coal or they may be produced by fermentation or they may be manufactured from petroleum fractions in excess supply. The aromatic hydrocarbons produced may be used to blend with gasoline, or they may be separated and used as petrochemicals or as solvents. Thus, in one aspect, the present invention affords a novel means for producing hydrocarbon petrochemicals and fuels.

DESCRIPTION OF SPECIFIC EMBODIMENTS

It is contemplated that any monohydric alcohol having from 1 to 4 carbon atoms or ethers derived from these alcohols may be used as feed to the process of this invention. Thus, methanol, ethanol, n-propanol, iso-propanol, n-butanol, sec-butanol and isobutanol may be used either alone or in admixture with one another or in admixture with the above compounds. Likewise, mixed ethers derived from these alcohols, such as methyl-ethyl ether, may similarly be used. Particularly preferred feeds are methanol, dimethyl ether and mixtures thereof.

In accordance with the present invention, such feed is brought into contact, under conversion conditions, with a catalyst comprising a crystalline aluminosilicate zeolite having a crystal size of at least about 1 micron, a silica to alumina ratio of at least about 12 and a constraint index within the approximate range of 1 to 12.

The zeolites herein described are members of a novel class of zeolites exhibiting some unusual properties. These zeolites induce profound transformations of aliphatic hydrocarbons to aromatic hydrocarbons in commercially desirable yields and are generally highly effective in conversion reactions involving aromatic hydrocarbons. Although they have unusually low alumina contents, i.e. high silica to alumina ratios, they are very active even when the silica to alumina ratio exceeds 30. The activity is surprising since catalytic activity is generally attributed to framework aluminum atoms and cations associated with these aluminum atoms. These zeolites retain their crystallinity for long periods in spite of the presence of steam at high temperature which induces irreversible collapse of the framework of other zeolites, e.g. of the X and A type. Furthermore, carbonaceous deposits, when formed, may be removed by burning at higher than usual temperatures to restore activity. In many environments the zeolites of this class exhibit very low coke forming capability, conducive to very long times on stream between burning regenerations.

An important characteristic of the crystal structure of this class of zeolites is that it provides constrained access to, and egress from the intracrystalline free space by virtue of having a pore dimension greater than about 5 Angstroms and pore windows of about a size such as would be provided by 10-membered rings of oxygen atoms. It is to be understood, of course, that these rings are those formed by the regular disposition of the tetrahedra making up the anionic framework of the crystalline aluminosilicate, the oxygen atoms themselves being bonded to the silicon or aluminum atoms at the centers of the tetrahedra. Briefly, the preferred type zeolites useful in this invention possess, in combination: a silica to alumina ratio of at least about 12; and a structure providing constrained access to the crystalline free space.

The silica to alumina ratio referred to may be determined by conventional analysis. This ratio is meant to represent, as closely as possible, the ratio in the rigid anionic framework of the zeolite crystal and to exclude aluminum in the binder or in cationic or other form within the channels. Although zeolites with a silica to alumina ratio of at least 12 are useful, it is preferred to use zeolites having higher ratios of at least about 30. Such zeolite, after activation, acquire an intracrystalline sorption capability for normal hexane which is greater than that for water, i.e. they exhibit "hydrophobic" properties. It is believed that this hydrophobic character is advantageous in the present invention.

The type zeolites useful in this invention freely sorb normal hexane and have a pore dimension greater than about 5 Angstroms. In addition, the structure must provide constrained access to larger molecules. It is sometimes possible to judge from a known crystal structure whether such constrained access exists. For example, if the only pore windows in a crystal are formed by 8-membered rings of oxygen atoms, then access by molecules of larger cross-section than normal hexane is excluded and the zeolite is not of the desired type. Windows of 10-membered rings are preferred, although, in some instances, excessive puckering or pore blockage may render these catalysts ineffective. Twelve-membered rings do not generally appear to offer sufficient constraint to produce the advantageous conversions, although puckered structures exist such as TMA offretite which is a known effective zeolite. Also, structures can be conceived, due to pore blockage or other cause, that may be operative.

Rather than attempt to judge from crystal structure whether or not a catalyst possesses the necessary constrained access, a simple determination of the "constraint index" may be made by passing continuously a mixture of an equal weight of normal hexane and 3-methylpentane over a small sample, approximately 1 gram or less, of zeolite at atmospheric pressure according to the following procedure. A sample of the zeolite, in the form of pellets or extrudate, is crushed to a particle size about that of coarse sand and mounted in a glass tube. Prior to testing, the zeolite is treated with a stream of air at 1000° F. for at least 15 minutes. The zeolite is then flushed with helium and the temperature adjusted between 550° F. and 950° F. to give an overall conversion between 10% and 60%. The mixture of hydrocarbons is passed at 1 liquid hourly space velocity (i.e., 1 volume of liquid hydrocarbon per volume of zeolite per hour) over the zeolite with a helium dilution to give a helium to total hydrocarbon mole ratio of 4:1. After 20 minutes on stream, a sample of the effluent is taken and analyzed, most conveniently by gas chromatography, to determine the fraction remaining unchanged for each of the two hydrocarbons.

The "constraint index" is calculated as follows:

$$\text{Constraint Index} = \frac{\log_{10} (\text{fraction of n-hexane remaining})}{\log_{10} (\text{fraction of 3-methylpentane remaining})}$$

The constraint index approximates the ratio of the cracking rate constants for the two hydrocarbons. Catalysts suitable for the present invention are those having a constraint index in the approximate range of 1 to 12. Constraint index (CI) values for some typical catalysts are:

| CAS | C.I. |
|---|---|
| ZSM-5 | 8.3 |
| ZSM-11 | 8.7 |
| ZSM-12 | 2 |
| ZSM-38 | 2 |
| ZSM-35 | 4.5 |
| TMA Offretite | 3.7 |
| Beta | 0.6 |
| ZSM-4 | 0.5 |
| H-Zeolon | 0.5 |
| REY | 0.4 |
| Amorphous Silica-Alumina | 0.6 |
| Erionite | 38 |

It is to be realized that the above constraint index values typically characterize the specified zeolites but that such are the cumulative result of several variables used in determination and calculation thereof. Thus, for a given zeolite depending on the temperature employed within the aforenoted range of 550° F. to 950° F., with accompanying conversion between 10% and 60%, the constraint index may vary within the indicated approximate range of 1 to 12. Likewise, other variables such as the crystal size of the zeolite, the presence of possibly occluded contaminants and binders intimately combined with the zeolite may affect the constraint index. It will accordingly be understood by those skilled in the art that the constraint index, as utilized herein, while affording a highly useful means for characterizing the zeolites of interest is approximate, taking into consideration the manner of its determination, with the probability, in some instances, of compounding variable extremes. However, in all instances, at a temperature within the above-specified range of 550° F. to 950° F., the constraint index will have a value for any given zeolite of interest herein within the approximate range of 1 to 12.

The class of zeolites defined herein is exemplified by ZSM-5, ZSM-11, ZSM-12, ZSM-35, ZSM-38, and other similar materials. U.S. Patent 3,702,886 describing and claiming ZSM-5 is incorporated herein by reference.

ZSM-11 is more particularly described in U.S. Patent 3,709,979, the entire contents of which are incorporated herein by reference.

ZSM-12 is more particularly described in U.S. Patent 3,832,449, the entire contents of which are incorporated herein by reference.

ZSM-38 is more particularly described in U.S. Application Ser. No. 528,060, filed Nov. 29, 1974. This zeolite can be identified, in terms of mole ratios of oxides and in the anhydrous state, as follows:

$$(0.3\text{-}2.5)R_2O : (0\text{-}0.8)M_2O : Al_2O_3 : 8 SiO_2$$

wherein R is an organic nitrogen-containing cation derived from a 2-(hydroxyalkyl) trialkylammonium compound and M is an alkali metal cation, and is characterized by a specified X-ray powder diffraction pattern.

In a preferred synthesized form, the zeolite has a formula, in terms of mole ratios of oxides and in the anhydrous state, as follows:

$$(0.4\text{-}2.5)R_2O : (0\text{-}0.6) M_2O : Al_2O_3 : xSiO_2$$

wherein R is an organic nitrogen-containing cation derived from a 2-hydroxyalkyl)trialkylammonium compound, wherein alkyl is methyl, ethyl or a combination thereof, M is an alkali metal, especially sodium, and x is from greater than 8 to about 50.

The synthetic ZSM-38 zeolite possesses a definite distinguishing crystalline structure whose X-ray diffraction pattern shows substantially the significant lines set forth in Table I. It is observed that this X-ray diffraction pattern (significant lines) is similar to that of natural ferrierite with a notable exception being that natural ferrierite patterns exhibit a significant line at 11.33A.

TABLE I

| d(A) | I/I₀ |
|---|---|
| 9.8 ± 0.20 | Strong |
| 9.1 ± 0.19 | Medium |
| 8.0 ± 0.16 | Weak |
| 7.1 ± 0.14 | Medium |
| 6.7 ± 0.14 | Medium |
| 6.0 ± 0.12 | Weak |
| 4.37 ± 0.09 | Weak |
| 4.23 ± 0.09 | Weak |
| 4.01 ± 0.08 | Very Strong |
| 3.81 ± 0.8 | Very Strong |
| 3.69 ± 0.07 | Medium |
| 3.57 ± 0.07 | Very Strong |
| 3.51 ± 0.07 | Very Strong |
| 3.34 ± 0.07 | Medium |
| 3.17 ± 0.06 | Strong |
| 3.08 ± 0.06 | Medium |
| 3.00 ± 0.06 | Weak |
| 2.92 ± 0.06 | Medium |
| 2.73 ± 0.06 | Weak |
| 2.66 ± 0.05 | Weak |
| 2.60 ± 0.05 | Weak |
| 2.49 ± 0.05 | Weak |

A further characteristic of ZSM-38 is its sorptive capacity providing said zeolite to have increased capacity for 2-methylpentane (with respect to n-hexane sorption by the ratio n-hexane/2-methyl-pentane) when compared with a hydrogen form of natural ferrierite resulting from calcination of an ammonium exchanged form. The characteristic sorption ratio n-hexane/2-methylpentane for ZSM-38 (after calcination at 600° C.) is less than 10, whereas that ratio for the natural ferrierite is substantially greater than 10, for example, as high as 34 or higher.

Zeolite ZSM-38 can be suitably prepared by preparing a solution containing sources of an alkali metal oxide, an oxide of aluminum, an oxide of silicon and water and having a composition, in terms of mole ratios of oxides, falling within the following ranges:

| R+ | Broad | Preferred |
|---|---|---|
| R+ + M+ | 0.2–1.0 | 0.3–0.9 |
| OH⁻/SiO₂ | 0.05–0.5 | 0.07–0.49 |
| H₂O/OH⁻ | 41–500 | 100–250 |
| SiO₂/Al₂O₃ | 8.8–200 | 12–60 | wherein R is an organic nitrogen-containing cation derived from a 2-hydroxyalkyl) trialkylammonium compound and M is an alkali metal ion, and maintaining the mixture until crystals of the zeolite are formed. (The quantity of OH⁻ is calculated only from the inorganic sources of alkali without any organic base contribution). Thereafter, the crystals are separated from the liquid and recovered. Typical reaction conditions consist of heating the foregoing reaction mixture to a temperature of from about 90° C. to about 400° C. for a period of time of from about 6 hours to about 100 days. A more preferred temperature range is from about 150° C. to abut 400° C. with the amount of time at a temperature in such range being from about 6 hours to about 80 days.

The digestion of the gel particles is carried out until crystals form. The solid product is separated from the reaction medium, as by cooling the whole to room temperature, filtering and water washing. The crystalline product is thereafter dried, e.g. at 230° F. for from about 8 to 24 hours.

(0.3–2.5)R₂O : (0–0.8)M₂O : Al₂O₃ : 8 SiO₂ wherein R is an organic nitrogen-containing cation derived from ethylenediamine or pyrrolidine and M is an alkali metal cation, and is characterized by a specified X-ray powder diffraction pattern.

In a preferred synthesized form, the zeolite has a formula, in terms of mole ratios of oxides and in the anhydrous state, as follows:

(0.4–2.5)R₂O : (0–0.6) M₂O : Al₂O₃ : xSiO₂ wherein R is an organic nitrogen-containing cation derived from ethylenediamine or pyrrolidine, M is an alkali metal, especially sodium, and x is from greater than 8 to about 50.

The synthetic ZSM-35 zeolite possesses a definite distinguishing crystalline structure whose X-ray diffraction pattern shows substantially the significant lines set forth in Table II. It is observed that this X-ray diffraction pattern (with respect to significant lines) is similar to that of natural ferrierite with a notable exception being that natural ferrierite patterns exhibit a significant line at 11.33A. Close examination of some individual samples of ZSM-35 may show a very weak line at 11.3–11.5A. This very weak line, however, is determined not to be a significant line for ZSM-35.

TABLE II

| d(A) | I/Io |
|---|---|
| 9.6 ± 0.20 | Very Strong – Very Very Strong |
| 7.10 ± 0.15 | Medium |
| 6.98 ± 0.14 | Medium |
| 6.64 ± 0.14 | Medium |
| 5.78 ± 0.12 | Weak |
| 5.68 ± 0.12 | Weak |
| 4.97 ± 0.10 | Weak |
| 4.58 ± 0.09 | Weak |
| 3.99 ± 0.08 | Strong |
| 3.94 ± 0.08 | Medium Strong |
| 3.85 ± 0.08 | Medium |
| 3.78 ± 0.08 | Strong |
| 3.74 ± 0.08 | Weak |
| 3.66 ± 0.07 | Medium |
| 3.54 ± 0.07 | Very Strong |
| 3.48 ± 0.07 | Very Strong |
| 3.39 ± 0.07 | Weak |
| 3.32 ± 0.07 | Weak Medium |
| 3.14 ± 0.06 | Weak Medium |
| 2.90 ± 0.06 | Weak |
| 2.85 ± 0.06 | Weak |
| 2.71 ± 0.05 | Weak |
| 2.65 ± 0.05 | Weak |
| 2.62 ± 0.05 | Weak |
| 2.58 ± 0.05 | Weak |
| 2.54 ± 0.05 | Weak |
| 2.48 ± 0.05 | Weak |

A further characteristic of ZSM-35 is its sorptive capacity proving said zeolite to have increased capacity for 2-methylpentane (with respect to n-hexane sorption by the ratio n-hexane/2-methylpentane) when compared with a hydrogen form of natural ferrierite resulting from calcination of an ammonium exchanged form. The characteristic sorption ratio n-hexane/2-methylpentane for ZSM-35 (after calcination at 600° C.) is less than 10, whereas that ratio for the natural ferrierite is substantially greater than 10, for example, as high as 34 or higher.

Zeolite ZSM-35 can be suitably prepared by preparing a solution containing sources of an alkali metal oxide, preferably sodium oxide, an organic nitrogen-containing oxide, an oxide of aluminum, an oxide of silicon and water and having a composition, in terms of mole ratios of oxides, falling within the following ranges;

| R+ | Broad | Preferred |
|---|---|---|
| R+ + M+ | 0.2-1.0 | 0.3-0.9 |
| OH⁻/SiO₂ | 0.05-0.5 | 0.07-0.49 |
| H₂O/OH⁻ | 41-500 | 100-250 |
| SiO₂/Al₂O₃ | 8.8-200 | 12-60 | wherein R is an organic nitrogen-containing cation derived from pyrrolidine or ethylenediamine and M is an alkali metal ion, and maintaining the mixture until crystals of the zeolite are formed. (The quantity of OH- is calculated only from the inorganic sources of alkali without any organic base contribution). Thereafter, the crystals are separated from the liquid and recovered. Typical reaction conditions consist of heating the foregoing reaction mixture to a temperature of from about 90° C. to about 400° C. for a period of time of from about 6 hours to about 100 days. A more preferred temperature range is from about 150° C. to about 400° C. with the amount of time at a temperature in such range being from about 6 hours to about 80 days.

The digestion of the gel particles is carried out until crystals form. The solid product is separated from the reaction medium, as by cooling the whole to room temperature, filtering and water washing. The crystalline product is dried, e.g. at 230° F., for from about 8 to 24 hours.

The specific zeolites described, when prepared in the presence of organic cations, are catalytically inactive, possibly because the intracrystalline free space is occupied by organic cations from the forming solution. They may be activated by heating in an inert atmosphere at 1000° F. for 1 hour, for example, followed by base exchange with ammonium salts followed by calcination at 1000° F. in air. The presence of organic cations in the forming solution may not be absolutely essential to the formation of this type zeolite; however, the presence of these cations does appear to favor the formation of this special type of zeolite. More generally, it is desirable to activate this type catalyst by base exchange with ammonium salts followed by calcination in air at about 1000° F. for from about 15 minutes to about 24 hours.

Natural zeolites may sometimes be converted to this type zeolite catalyst by various activation procedures and other treatments such as base exchange, steaming, alumina extraction and calcination, in combinations. Natural minerals which may be so treated include ferrierite, brewsterite, stilbite, dachiardite, epistilbite, heulandite, and clinoptilolite. The preferred crystalline aluminosilicates are ZSM-5, ZSM-11, ZSM-12, ZSM-38 and ZSM-35, with ZSM-5 particularly preferred.

The catalysts of this invention may be in the hydrogen form or they may be base exchanged or impregnated to contain ammonium or a metal cation complement. It is desirable to calcine the catalyst after base exchange. The metal cations that may be present include any of the cations of the metals of Groups I through VIII of the periodic table. However, in the case of Group IA metals, the cation content should in no case be so large as to effectively inactivate the catalyst.

In a preferred aspect of this invention, the catalysts hereof are selected as those having a crystal framework density, in the dry hydrogen form, of not substantially below about 1.6 grams per cubic centimeter. It has been found that zeolites which satisfy all three of these criteria are most desired because they tend to maximize the production of gasoline boiling range hydrocarbon products. Therefore, the preferred catalysts of this invention are those having a constraint index as defined above of about 1 to about 12, a silica to alumina ratio of at least about 12 and a dried crystal density of not less than about 1.6 grams per cubic centimeter. The dry density for known structures may be calculated from the number of silicon plus aluminum atoms per 1000 cubic Angstroms, as given, e.g., on Page 19 of the article on Zeolite Structure by W. M. Meier. This paper, the entire contents of which are incorporated herein by reference, is included in "Proceedings of the Conference on Molecular Sieves, London, April 1967," published by the Society of Chemical Industry, London, 1968. When the crystal structure is unknown, the crystal framework density may be determined by classical pyknometer techniques. For example, it may be determined by immersing the dry hydrogen form of the zeolite in an organic solvent which is not sorbed by the crystal. It is possible that the unusual sustained activity and stability of this class of zeolites is associated with its high crystal anionic framework density of not less than about 1.6 grams per cubic centimeter. This high density, of course, must be associated with a relatively small amount of free space within the crystal, which might be expected to result in more stable structures. This free space, however, is important as the locus of catalytic activity.

Crystal framework densities of some typical zeolites are:

| Zeolite | Void Volume | Framework Density |
|---|---|---|
| Ferrierite | 0.28 cc/cc | 1.76 g/cc |
| Mordenite | .28 | 1.7 |
| ZSM-5, -11 | .29 | 1.79 |
| Dachiardite | .32 | 1.72 |
| L | .32 | 1.61 |
| Clinoptilolite | .34 | 1.71 |
| Laumontite | .34 | 1.77 |
| ZSM-4 (Omega) | .38 | 1.65 |
| Heulandite | .39 | 1.69 |
| P | .41 | 1.57 |
| Offretite | .40 | 1.55 |
| Levynite | .40 | 1.54 |
| Erionite | .35 | 1.51 |
| Gmelinite | .44 | 1.46 |
| Chabazite | .47 | 1.45 |
| A | .5 | 1.3 |
| Y | .48 | 1.27 |

The crystal size of the synthesized zeolite has been found to be an important factor affecting the desired conversion of the described alcohol and/or ether charge stock to low molecular weight olefins and para-xylene. The crystal size of the above-described crystalline aluminosilicate zeolite employed in the process of the invention is at least about 1 micron, being in the approximate range of 1 – 20 microns and particularly in the range of 1 – 6 microns. With the use of crystals within such size range, distinctly higher selectivity for production of the desired $C_2$–$C_3$ olefins and para-xylene has been observed as compared with comparable use of smaller size crystals.

When synthesized in the alkali metal form, the zeolite is conveniently converted to the hydrogen form, generally by intermediate formation of the ammonium form as a result of ammonium ion exchange and calcination of the ammonium form to yield the hydrogen form. In general, it is contemplated that more than 50 percent and preferably more than 75 percent of the cationic sites of the crystalline aluminosilicate zeolite, above described, will be occupied by hydrogen ions. In addition to the hydrogen form, other forms of the zeolite wherein the original alkali metal has been reduced to less than about 1.5 percent by weight may be used. Thus, the original alkali metal of the zeolite may be replaced by ion exchange with other suitable ions of Groups IB to VIII of the Periodic Table including, by way of example, nickel, zinc, calcium or rare earth metals.

It may be desirable in some instances to incorporate the zeolite in another material resistant to the temperatures and other conditions employed in the conversion process. Such matrix materials are to be distinguished from the aforenoted inert diluents and include synthetic or naturally occurring substances as well as inorganic materials such as clay, alumina or other metal oxides. The latter may be either naturally occurring or in the form of gelatinous precipitates or gels including mixtures of silica and metal oxides. Naturally occurring clays which can be composited with the zeolite include those of the montmorillonite and kaolin families, which families include the sub-bentonites and the kaolins commonly known as Dixie, McNamee-Georgia and Florida clays or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, the zeolites employed herein may be composited with a porous matrix material, such as alumina, silica-alumina, silica-magnesia, silica-zirconia, silica-thoria, silica-berylia, silica-titania as well as ternary compositions, such as silica-alumina-thoria, silica-alumina-zieconia, silica-alumina-magnesia and silica-magnesia-zirconia. The matrix may be in the form of a cogel. The relative proportion of finely divided zeolite and inorganic oxide gel matrix may vary widely with the zeolite content ranging from between 1 to about 99 percent by weight and more usually in the range of about 5 to about 80 percent by weight of the composite. In the process of this invention, the feed consisting essentially of one or more of the lower alcohols or ethers derived therefrom is contacted with the above described catalyst bed at a temperature of about 500° F to about 950° F. and preferably about 600° F. to about 850° F,; a contact time equivalent to or the same as a weight hourly space velocity (WHSV) of about 1 to about 100 preferably about 2 to about 40, it being understood that WHSV signifies pounds of feed per pound of zeolite per hour; and at an absolute pressure of about 0.2 to about 50 atmospheres, preferably between about 1 and about 30 atmospheres.

The reaction product effluent from the process of the invention contains steam and a hydrocarbon mixture particularly rich in the light olefins, ethylene and propylene, and aromatic hydrocarbons with high selectivity for para-xylene. Generally, a major fraction of the total olefins, calculated on a mol basis, is ethylene plus propylene. The predominant aromatic hydrocarbons are monocyclic hydrocarbons, notably $C_8$ and $C_9+$ aromatics with a high proportion of para-xylene. Thus, the predominant hydrocarbons are all valuable petrochemicals. The steam and hydrocarbons are separated from one another by methods well known in the art.

The particular proportions of olefins and aromatics may be varied by selecting reaction conditions within the purview specified above, olefins being favored by lower temperatures and in general by less severe conversion conditions. Thus, it is a feature and advantage of the process described herein that the nature and composition of the reaction product mixture can be readily varied within the confines noted above to satisfy changes of demand.

Catalyst deactivated by coke deposited during the process may be regenerated by calcining in an oxygen-containing atmosphere, e.g. air, at an elevated temperature within the approximate range of 600° to 1200° F. for a period of between about 1 and about 30 hours.

The following examples will serve to illustrate the process of this invention without limiting the same:

EXAMPLE 1

42.2 pounds of Q-Brand sodium silicate were mixed with 52.8 pounds of water. The resulting solution was designated Solution A. 1.35 pounds of commercial grade aluminum sulfate ($Al_2(SO_4)_3 \cdot 14\ H_2O$)), 15.84 pounds of commercial grade NaCl, and 3.52 pounds of $H_2SO_4$ (96.06 wt % $H_2SO_4$) were mixed with 72.2 pounds of water. The resulting solution was designated Solution B. Solution A and Solution B were mixed simultaneously in a nozzle and sprayed into an autoclave equipped with a paddle agitator. 2.84 pounds of tri-n-propylamine and 2.44 pounds of n-propyl bromide were added to the contents of the autoclave. The mixture was reacted at 316° F. with 121 rpm agitation. After 14.1 hours at 316° F., the solid product was analyzed by x-ray diffraction and found to be 100% ZSM-5.

A 10 gram sample of the above ZSM-5 was contacted with 500 ml. of 1 N $NH_4Cl$ solution. Three ion exchange steps were carried out, the first at 100° C. for 2 hours, the second at room temperature for 18 hours and the third at 100° C. for 3 hours. The exchanged product was thereafter calcined 1° C/minute to a temperature of 1000° F. and held at such temperature for 10 hours. The resulting HZSM-5 had a crystallite size of 1–2 microns.

EXAMPLE 2

A 50 milligram sample of the catalyst of Example 1, in finely divided form capable of passing through a 100 mesh screen (U.S. Standard), was intimately mixed with 2.5 grams of vycor of 20 to 50 mesh size (U.S. Standard Screen).

Methanol was passed through this catalyst bed maintained at a temperature of 650° F. at a weight hourly space velocity of 10. Conversion of methanol to hydrocarbon was 58 percent.

The resulting hydrocarbon conversion product, upon analysis, was found to contain the following:

| Component | Weight Percent |
|---|---|
| Ethylene | 26 |
| Propylene | 24 |
| Butenes | 10 |
| $C_8$ Aromatics | 7 |
| $C_9^+$ Aromatics | 4 |
| $C_1$-$C_4$ Paraffins | 8 |
| $C_5^+$ Paraffins and Olefins | 21 |

The concentration of para-xylene in the xylene fraction was about 80 weight percent.

EXAMPLE 3

A sample of the catalyst of Example 1 in finely divided form capable of passing through a 100 mesh screen (U.S. Standard) was intimately mixed with alumina, previously calcined at 1000° F., of mesh (U.S. Standard Screen) size to provide a mixture containing 10 weight percent HZSM-5 and 90 weight percent alumina. The resulting mixture was pelleted and sized to 14/30 mesh (U.S. Standard Screen).

Methanol was passed through a bed of this catalyst maintained at a temperature of 650° F. at a weight hourly space velocity of 10-50. Conversion of methanol to hydrocarbon was 60 percent.

The resulting hydrocarbon conversion product, upon analysis, was found to contain the following:

| Component | Weight Percent |
| --- | --- |
| Ethylene | 27.0 |
| Propylene | 26.2 |
| Butene | 11.0 |
| Methane | 0.5 |
| Propane | 2.2 |
| Butanes | 4.6 |
| $C_4^+$ (Non-aromatics) | 20.4 |
| Aromatics | 8.1 |

The concentration of para-xylene in the xylene fraction was about 91 weight percent.

EXAMPLE 4 – 5

In these two examples, a catalyst sample of 1 gram in the form of 14–30 mesh particles was placed into a vertical flow reactor. Methanol was passed through the reactor at a temperature of 350° C, a pressure of 1 atmosphere at a liquid hourly space velocity of 1.2 – 1.3.

The catalyst in Example 4 was a microcrystalline HZSM-5 with a crystal size of 0.02–0.05 micron. The catalyst in Example 5 was a large crystal HZSM-5 with a crystal size of 1–2 microns as determined by scanning electron microscopy.

Conversion of methanol to hydrocarbon and water as well as ethylene selectivities are shown in the following table:

|  | Example 4 | Example 5 |
| --- | --- | --- |
| Crystal Size (micron) | 0.02 – 0.05 | 1 – 2 |
| Methanol Conversion, % | 98 | 98 |
| Ethylene Selectivity |  |  |
| % of Hydrocarbon | 0.6 | 14 |

It will be seen from the above data that while only traces of ethylene are found with the microcrystalline catalyst, the large crystal size catalyst unexpectedly produced an appreciable yield of ethylene at the same conversion.

It is to be understood that the foregoing description is merely illustrative of preferred embodiments of the invention of which many variations may be made by those skilled in the art within the scope of the following claims without departing from the spirit thereof.

I claim:

1. A process for producing hydrocarbons which comprises contacting, under conversion conditions, a charge consisting essentially of one or more lower monohydric alcohols having up to four carbon atoms, the ethers derived therefrom or mixtures of said alcohols and ethers with a catalyst comprising a crystalline aluminosilicate zeolite having a crystal size of at least about 1 micron, a silica to alumina ratio of about 12 and a constraint index within the approximate range of 1 to 12 to yield a reaction product mixture comprising $C_2$-$C_3$ olefins, monocyclic aromatic hydrocarbons and water and recovering said hydrocarbons.

2. The process of claim 1 wherein said conversion conditions include a temperature of from about 500° F. to about 950° F., a pressure from about 0.2 to about 50 atmospheres and a weight hourly space velocity of between about 1 and about 100.

3. The process of claim 1 wherein said conversion conditions include a temperature of from about 600° F. to about 850° F., a pressure from about 1 to about 30 atmospheres and a weight hourly space velocity of between about 2 and about 40.

4. The process of claim 1 wherein said charge is methanol, dimethyl ether or mixtures thereof.

5. The process of claim 1 wherein said crystalline aluminosilicate zeolite is ZSM-5.

6. The process of claim 1 wherein said crystalline aluminosilicate zeolite is ZSM-5 predominately in the hydrogen form.

7. The process of claim 1 wherein the crystal size of said crystalline aluminosilicate zeolite is within the approximate range of 1 to 20 microns.

8. The process of claim 1 wherein the crystal size of said crystalline aluminosilicate zeolite is within the approximate range of 1 to 6 microns.

9. The process of claim 5 wherein the ZSM-5 is present in combination with a binder therefor.

* * * * *